(12) United States Patent
Hirschel et al.

(10) Patent No.: US 8,298,175 B2
(45) Date of Patent: Oct. 30, 2012

(54) ADMINISTERING DEVICE WITH BLOCKABLE ACTUATION ELEMENT

(75) Inventors: Juerg Hirschel, Aarau (CH); Celine Kaenel-Jost, Zurich (CH); Ulrich Moser, Heimiswil (CH); Annette Drunk, Bern (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 51 days.

(21) Appl. No.: 12/853,735

(22) Filed: Aug. 10, 2010

(65) Prior Publication Data

US 2011/0077588 A1   Mar. 31, 2011

Related U.S. Application Data

(63) Continuation of application No. PCT/CH2009/000042, filed on Feb. 4, 2009.

(30) Foreign Application Priority Data

Feb. 11, 2008 (CH) ........................................ 0189/08

(51) Int. Cl.
*A61M 37/00* (2006.01)

(52) U.S. Cl. .......................................................... 604/82
(58) Field of Classification Search ..................... 604/82
See application file for complete search history.

(56) References Cited

U.S. PATENT DOCUMENTS

| 6,607,508 B2 * | 8/2003 | Knauer ........................ 604/131 |
| 2006/0189938 A1 | 8/2006 | Hommann et al. |
| 2009/0259181 A1 | 10/2009 | Moser |

FOREIGN PATENT DOCUMENTS

| DE | 10 2005 007 614 | 8/2006 |
| DE | 10 2006 017209 | 10/2007 |
| WO | WO 2007/051331 | 5/2007 |

* cited by examiner

*Primary Examiner* — Nicholas Lucchesi
*Assistant Examiner* — Jason Flick
(74) *Attorney, Agent, or Firm* — Dorsey & Whitney LLP; David E. Bruhn, Esq.

(57) ABSTRACT

An apparatus for administering a fluid product, including a housing, an administering mechanism accommodated in the housing, an actuation element for actuating the administering mechanism, a receptacle for holding the fluid product, and a lock for releasably locking the actuation element, wherein the receptacle is rotatable relative to the housing and the lock can be moved from a locked position to an unlocked position by rotating the receptacle.

13 Claims, 7 Drawing Sheets

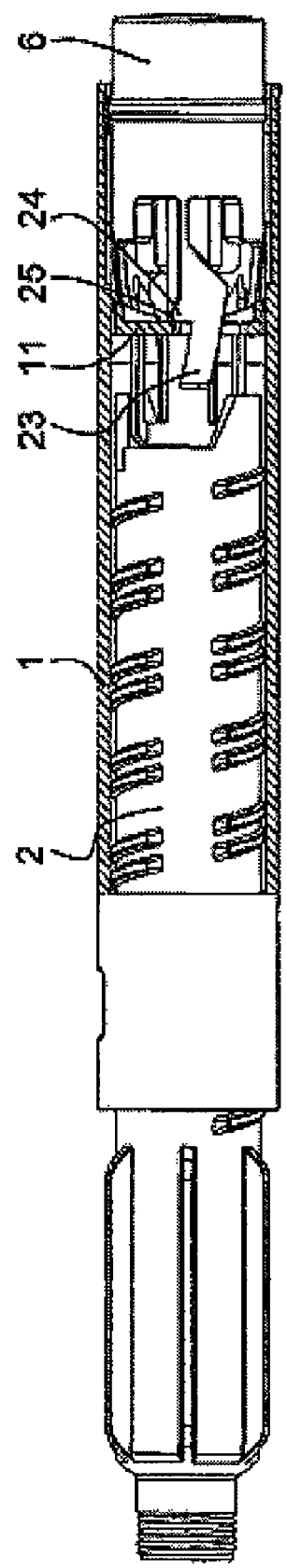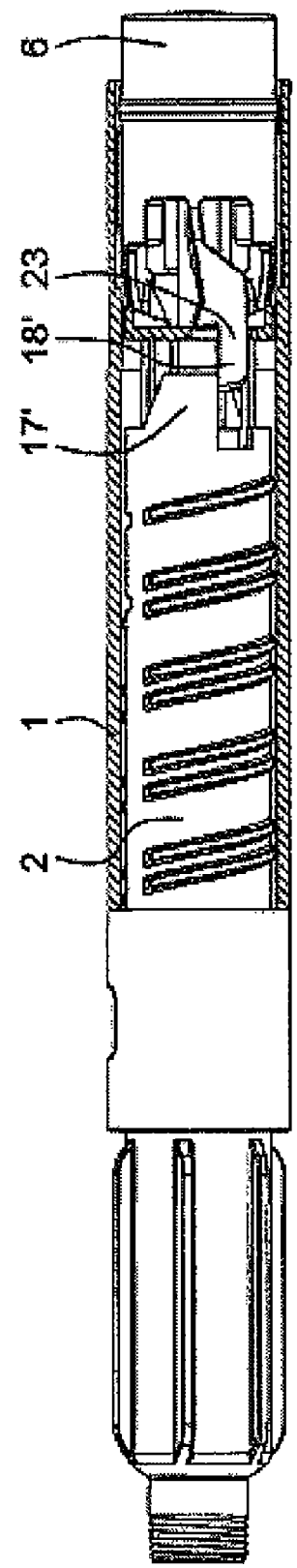

ADMINISTERING DEVICE WITH BLOCKABLE ACTUATION ELEMENT

CROSS-REFERENCED RELATED APPLICATIONS

This application is a continuation of International Patent Application No. PCT/CH2009/000042 filed Feb. 4, 2009, which claims priority to Swiss Patent Application No. 189/08 filed Feb. 11, 2008, the entire contents of each are incorporated herein by reference.

BACKGROUND

The present invention relates to devices for administering, injecting, infusing, delivering or dispensing a substance, and to methods of making and using such devices. More particularly, it relates to a device for administering a fluid or liquid product or substance, e.g. fluid medicaments, pharmaceuticals or cosmetics. More particularly, it relates to a device for administering a fluid product that is to be mixed in a two-chamber carpule (which also may be thought of and/or referred to as an ampoule, container, or the like) before use.

In the treatment of various diseases, e.g. diabetes, and in cases of impaired growth, injection devices or appliances, which may be called injections pens or simply pens, are used to inject a medicament in the form of a fluid product into the body tissue. Such pens can also be used for other pharmaceutical or cosmetic purposes. Typically, a pen comprises a housing, an administering mechanism accommodated at least partially in the housing, and a receptacle for receiving the fluid product, e.g. a carpule holder, which receives a carpule and which is supported by or attached to the housing to connect the carpule to the administering mechanism. Generally, the administering mechanism is composed of a mechanism that is able to drive or move a stopper in the carpule. Generally, at the end of the carpule holder and directed away from the mechanism, an injection needle unit is fitted which forms a fluid connection to the fluid product in the carpule. Typically, an injection pen comprises a trigger button, the actuation of which activates the administering mechanism, such that the medicament is ejected from the carpule through the injection needle. In the prior art, it is known to block or lock the trigger button or to cover it, or in some other way to safeguard against accidental triggering. The blocking or safety feature is overridden or released just before use of the injection pen to be able to carry out an injection.

Two-chamber carpules are often used in practice, these being provided, for example, for administration of hormone preparations. The two-chamber carpules have a first chamber with a lyophilized active substance, and a second chamber with a solvent. The active substance is dissolved in the solvent just before administration, by the solvent being conveyed into the chamber containing the active substance. These two-chamber carpules have two stoppers, which separate the two chambers from each other. During the mixing of the active substance, the two stoppers are moved inside the carpule in such a way that the solvent can run through a bypass into the chamber containing the active substance. Especially when using two-chamber carpules of this kind in an injection pen, it is important to ensure that no accidental or premature administration is initiated, since in such cases the medicament may not have been completely mixed.

SUMMARY

It is an object of the present invention to make available an administering device which minimizes or avoids the chance of accidental or premature actuation of the device and thus increases the safety of the device.

In one embodiment, the present invention comprises an apparatus for administering a substance, comprising a housing, an administering mechanism accommodated in the housing, an actuation element for actuating the administering mechanism, a receptacle for holding the substance, and a lock for releasably locking the actuation element, wherein the receptacle is rotatable relative to the housing and the lock can be unlocked by rotating the receptacle.

In one embodiment, the present invention comprises a device for administering a fluid product comprising a housing for receiving an administering mechanism, an actuation element for actuating the administering mechanism, a receptacle for receiving the fluid product, and a blocking mechanism (which also may be thought of and/or referred to as a lock) for blocking the actuation element. The housing of the device can have a sleeve-shaped configuration, such that the device has the shape of a pen or pencil. An aspect of the configuration of the housing is that the administering mechanism can be accommodated therein without its function being impaired. It is also possible for the housing to carry and/or include functional elements of the administering mechanism and, thus, form part of the administering mechanism.

In some embodiments, for example, the administering mechanism is composed of a mechanism generally comprising an advancing member, e.g. a piston rod, which can be advanced relative to the housing in the direction of the receptacle for the fluid product. There, it generally contacts a stopper in the receptacle, such that the movement of the advancing member also has the effect that the stopper in the receptacle is driven forward and the fluid product is discharged. The advancing member can be driven manually. However, it is also possible to provide a drive in the form of a pretensioned spring. Moreover, non-mechanical drives may be used, e.g. pneumatic drives.

The actuation element for actuating the administering mechanism is movable relative to the housing, to be able to act on the administering mechanism. The actuation element can protrude from the housing in the form of a button. However, it is also possible to arrange the actuation element laterally on the housing, e.g. in the form of a slide or lever. The actuation element can be used to activate the administering mechanism, e.g. the advancing member, directly, or a pretensioned spring element can be released from its pretensioning and then act in turn on the advancing member.

The fluid product is accommodated in the receptacle for receiving the fluid product. In some preferred embodiments, the fluid product is located or contained in a carpule or the like that can be inserted into the receptacle. Such carpules generally have a first end, closed off by a stopper, and a second end, closed off by a thin membrane through which a needle of an injection needle unit can be pushed for and/or during use. The receptacle with the carpule can be attached to the administering mechanism by inserting the receptacle into the housing or mounting it on the housing.

To block or lock the actuation element, a device for administering a fluid product in accordance with the present invention has a blocking mechanism (which also may be thought of and/or referred to as a lock). The blocking mechanism prevents the actuation of the actuation element and, consequently, the actuation of the administering mechanism when the blocking mechanism is locked or located in a blocking position. The blocking mechanism can be moved from the blocking position to a release (released or unlocked) position in which the actuation element can be actuated to administer the fluid product by the administering mechanism.

According to the present invention, the receptacle is mounted so as to be rotatable relative to the housing, the blocking mechanism being movable from the blocking position to the release position by rotation of the receptacle relative to the housing. The receptacle is in this case rotated, for example, about a longitudinal axis of the housing or of the receptacle. Thus, by the rotation of the receptacle, an injection pen in accordance with the present invention can be unlocked and the administering mechanism triggered using the actuation element.

Locking and unlocking of the blocking mechanism in accordance with the present invention is advantageous when using two-chamber carpules which, for the mixing procedure, are turned or screwed into the housing of the administering device. In this case it is possible, by the rotation, to trigger the mixing procedure in the two-chamber carpule and also to move the blocking mechanism to the release or unlocked position. It is also possible for the receptacle to be arranged on or in the housing by a bayonet coupling, which bayonet coupling is also established by a rotation movement. In this rotation too, according to the present invention, the blocking mechanism can at the same time be moved to a release position.

In some preferred embodiments, to move the blocking mechanism from the blocking position to the release position, the receptacle has an abutment and the blocking mechanism has a counter-abutment. The abutment of the receptacle and the counter-abutment of the blocking mechanism interact in such a way that, upon rotation of the receptacle relative to the housing, they contact each other and, upon further rotation of the receptacle, they entrain the blocking mechanism and move the latter from the blocking position to the release position. For this purpose, the blocking mechanism is rotatable, for example, relative to the housing in the circumferential direction of the housing.

As soon as the blocking mechanism is located in the released or unlocked position, the actuation element can be activated. In some preferred embodiments, in the release position of the blocking mechanism, the actuation element may be moved relative to the housing along the longitudinal axis of the housing. For example, an actuation button protruding from the housing at one end is pressed or pushed into the housing.

According to one embodiment of the present invention, the blocking mechanism is arranged on the actuation element. For example, the blocking mechanism and the actuation element can be structured as one piece. In this case, the blocking mechanism and the actuation element can be produced from a single section. However, it is also possible to subsequently secure the blocking mechanism on the actuation element. In one variant, the actuation element then moves along with the blocking mechanism when the blocking mechanism is moved from the blocking position to the release position. For example, the actuation element is rotated along with the rotation of the receptacle.

In another variant, the blocking mechanism may be a flexible arm. The flexible arm can deflect in the circumferential direction of an axis of the actuation element, that is to say it can bend away from its rest position in a direction of rotation about the longitudinal axis. In this embodiment, the flexible arm forms the counter-abutment of the blocking mechanism, which counter-abutment interacts with the abutment of the receptacle. As the receptacle rotates, its abutment contacts the flexible arm and deflects the arm from the rest position, as a result of which the blocking mechanism is moved to a release position.

In some preferred embodiments, the blocking or locking of the actuation element is effected by a blocking abutment on the blocking mechanism, which blocking abutment, in the blocking position, contacts a longitudinal abutment on the housing or a structure fixed to the housing in the longitudinal direction. A longitudinal abutment is to be understood as an abutment that blocks a movement along a longitudinal axis of the administering device. When the blocking abutment bears on the longitudinal abutment, the actuation element cannot be actuated in this longitudinal direction. The actuation element is therefore blocked against being pressed or pushed into the housing. This blocking is canceled by the deflection of the flexible arm, since the blocking abutment on the blocking mechanism is moved laterally away from the longitudinal abutment by the deflection of the flexible arm upon rotation of the receptacle. In the deflected position of the flexible arm, the blocking mechanism assumes a release or unlocked position. The blocking abutment can then be guided laterally past the longitudinal abutment in the longitudinal direction when the actuation element is moved into the housing.

In another embodiment of the present invention, the blocking mechanism is designed as a rotary element that can be rotated relative to the actuation element. In this case, the blocking mechanism has a blocking abutment which, in the blocking position, contacts a longitudinal abutment on the actuation element, on the housing, or a part fixed to the housing. In this embodiment, the actuation element is therefore not movable in the longitudinal direction of the housing relative to the blocking mechanism in the blocking position. If the longitudinal abutment is provided on the actuation element, the rotary element is mounted rotatably in the housing such that it is not movable relative to the housing in the longitudinal direction. By rotating the rotary element by the rotation of the receptacle, the blocking abutment is removed from the longitudinal abutment on the actuation element, and the blocking is canceled. The actuation element can then be moved in the longitudinal direction relative to the housing and to the rotary element.

If the longitudinal abutment is provided on the housing or on a part fixed to the housing, the rotary element is mounted rotatably in the housing such that, in the blocking position, it is rotatable relative to the housing but not longitudinally movable and, in the release position, can be moved in the longitudinal direction relative to the housing. The blocking thus acts between the blocking mechanism, in the form of the rotary element, and the housing. If the rotary element is rotated relative to the housing by the rotation of the receptacle, the blocking abutment is moved away from the longitudinal abutment on the housing or on the part fixed to the housing. The blocking mechanism can then be moved, together with the actuation element, relative to the housing in the longitudinal direction. Thus, in these variants too, the actuation element is prevented from being activated. The blocking mechanism and the rotary element are rotated by the rotation movement of the receptacle relative to the housing, by the abutment on the receptacle and the counter-abutment on the blocking mechanism. By this rotation, the abutment action between the blocking abutment of the blocking mechanism and the longitudinal abutment on the actuation element or on the housing or on the part fixed to the housing is canceled, and these abutments can be moved past one another in the longitudinal direction. Accordingly, in this position, the blocking mechanism is located in a release position in which the actuation element can be activated.

In some embodiments, it may be advantageous if the rotary element of the blocking mechanism is secured in the blocking position. Such securing can, for example, be afforded by a press fit or by a pretensioning of a spring element. Upon rotation of the receptacle, the rotary element is then pushed out of the press fit or deflected counter to the spring tension.

In some embodiments of the present invention, it is advantageous to provide a catch mechanism which locks the receptacle relative to the housing in the release position of the blocking mechanism. The locking action ensures that the receptacle does not rotate back in the opposite direction and cause the blocking mechanism to move from the release position back to a blocking position. Such a catch mechanism can, for example, be in the form of a snap-action or detent mechanism on the receptacle, which snaps into a recess on the housing.

The present invention is advantageous when using a two-chamber carpule in a device for administering a fluid product. The receptacle for the two-chamber carpule has a thread, and the housing has a matching thread. Thus, the receptacle can be turned or screwed into the housing. When using the two-chamber carpule, the screwing of the receptacle into the housing can be used to mix the components or constituents of the fluid product in the two-chamber carpule. By screwing the receptacle into the housing, a first stopper in the two-chamber carpule is pushed forward (i.e., distally), e.g. by the advancing member of the administering mechanism. The forward movement is transferred via the solvent in the first chamber to the second stopper which separates the solvent chamber from the active substance chamber. The two stoppers are moved uniformly until the second stopper has arrived at a bypass in the carpule wall, through which bypass the solvent can run from the solvent chamber into the active substance chamber. The first stopper is pushed forward until the solvent is in the first chamber, and until the first stopper comes to lie on the second stopper. The screwing-in of the two-chamber carpule is such that the blocking mechanism is moved from the blocking position to the release position as soon as all of the solvent has passed from the solvent chamber to the active substance chamber. By the catch mechanism, the receptacle is locked relative to the housing in the release position of the blocking mechanism, such that the administering device, in this position, is ready for an injection, that is to say the active substance has been mixed completely and the blocking of the administering device is canceled. As soon as an injection needle unit is fitted onto the receptacle, an injection can be performed. In this embodiment, it is advantageous that no separate maneuver is needed to unlock the blocking mechanism, and instead the blocking action is canceled by the necessary mixing of the two-chamber carpule.

BRIEF DESCRIPTION OF THE DRAWINGS

FIG. 7a is a detailed view of another embodiment of an administering device in a blocking position, and FIG. 7b is a detailed view of the administering device of FIG. 7a in a release or unlocked position.

DETAILED DESCRIPTION

Figure 1:
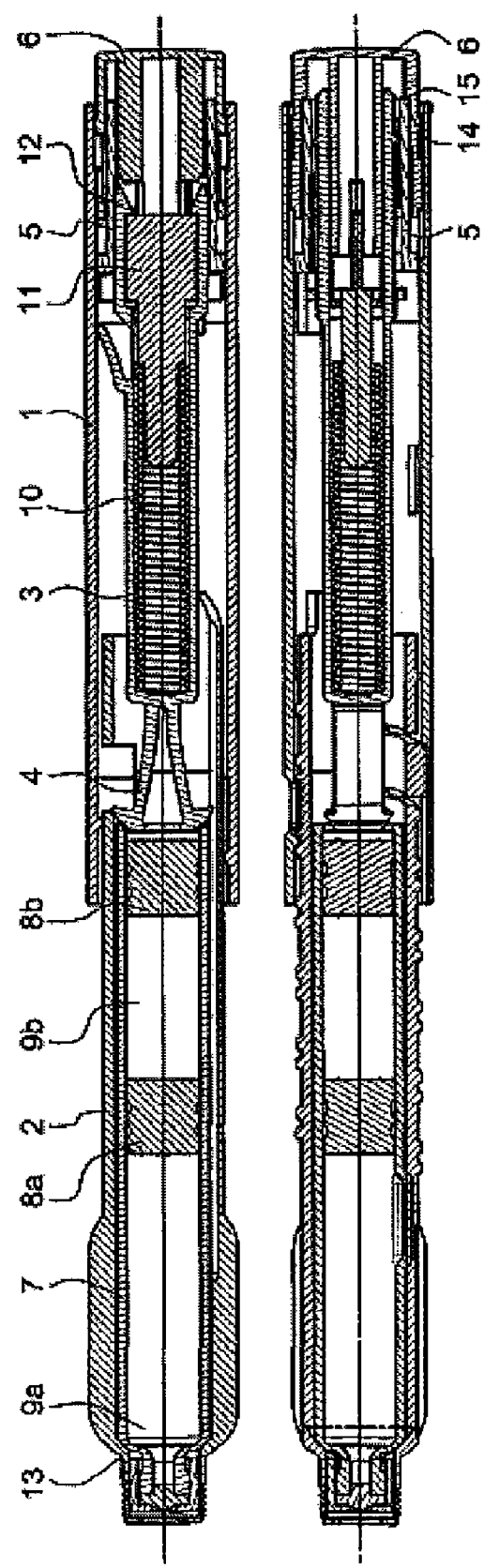
FIG. 1 depicts an embodiment of an administering device in accordance with the present invention in a starting state.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

FIGS. 1 to 6 show an embodiment of an administering device according to the present invention with a blocking mechanism, or lock, for blocking an actuation element. FIGS. 7a and 7b show another embodiment of a blocking mechanism for blocking an actuation element. Each of FIGS. 1 to 5 shows two views, of which the second view at the bottom is turned through 90° in relation to the first view at the top.

The administering device according to one embodiment of the present invention uses a two-chamber carpule as container for a fluid product. The fluid product is discharged from the carpule by a drive member being moved forward (distally) by a discharging spring. The product is therefore discharged automatically as soon as the discharging spring is activated. The administering device has a fixed dose, i.e. the discharge volume is fixed. The forward movement of the drive member is therefore also fixed and cannot be individually adjusted. The administering device is blocked or locked after a single discharge procedure and is discarded after the discharge procedure.

It should be clear to a person skilled in the art that a blocking mechanism or lock according to the present invention can be used equally advantageously in reusable administering devices, in devices with individual dosing or manual discharge, and also in devices with single-chamber carpules.

In the text below, the term distal (and terms front or forward) refer to the end of the administering device at which the fluid product is discharged, and the term proximal designates the opposite end (the rear or back end).

The administering device according to one embodiment of the present invention has a housing 1, a receptacle for receiving the fluid product or substance to be administered in the form of a carpule holder 2, a drive member 3 with a holding mechanism in the form of holding arms 4, a blocking mechanism in the form of a blocking ring 5, and an actuation element in the form of a trigger button 6.

A two-chamber carpule 7 is accommodated in the carpule holder 2. The two-chamber carpule has a first stopper 8a and a second stopper 8b. The second stopper 8b closes the two-chamber carpule at the proximal end. At the distal end, the two-chamber carpule has a narrowed area whose opening is closed off by a membrane. The membrane can be pierced by a needle of an injection needle unit. The injection needle unit is not shown in the figures. A first chamber 9a, in which a dry or lyophilized active substance is accommodated (not shown), is formed between the membrane and the first stopper 8a. A second chamber, in which the solvent for the active substance is stored, is formed between the first stopper 8a and the second stopper 8b.

The drive member 3 has a sleeve-shaped configuration. A drive spring 10, arranged in the inside of the drive member 3, is clamped between a distal abutment at the sleeve base of the drive member and a proximal abutment on an element 11 fixed to the housing. In the starting state in FIG. 1, the drive member 3 is held relative to the housing element 11 by snap-action arms 12, which releasably snap in behind an abutment of the housing element 11. At the distal end of the drive member 3, the holding arms 4 are mounted in such a way that they protrude or extend laterally from a longitudinal axis of the drive member in this starting position. In the embodiment depicted, two holding arms are shown spread apart from each other. It is of course also possible to provide three or more such holding arms 4. In the starting state in FIG. 1, the distal ends of the holding arms 4 abut against a proximal edge of the carpule 7. The holding arms 4 press the carpule 7 against a shoulder 13 of the carpule holder 2. The carpule 7 is therefore held in a defined (or certain or selected) position, relative to the carpule holder 2, by the holding mechanism in the from of the holding arms 4. This prevents the carpule from moving back and forth in the proximal and distal directions in the holder.

In the starting state in FIG. 1, the blocking ring 5 is located in a blocking position in which it blocks or prevents an actuation of the trigger button 6, i.e. the trigger button 6 cannot be pressed in the longitudinal direction into the housing 1. For this purpose, the blocking ring 5 has a blocking abutment 14, which rests on a counter-abutment 15 on the trigger button 6. By the blocking abutment 14 of the blocking ring 5 and the counter-abutment 15 of the trigger button 6 abutting or contacting each other, the trigger button 6 cannot be actuated, that is to say it cannot be pressed into the housing along the longitudinal axis of the housing. For this purpose, the blocking ring 5 is mounted fixedly relative to the housing in the longitudinal direction but can be rotated relative to the housing. The blocking abutment 14 can be formed, for example, by ribs or cams on the blocking ring or by the proximal edge of the blocking ring 5.

The blocking ring 15 has a sleeve-shaped configuration and surrounds the snap-action arms 12 of the drive member 3. In the starting state in FIG. 1, the inner circumferential surface of the blocking ring 5 bears on the outside of the snap-action arms 12 such that the arms cannot be released from their snap-in engagement behind the housing element 11. The blocking ring 5 thus blocks an actuation of the trigger button 6 and also a release of the snap-action arms 12. The starting state corresponds to a delivery or purchase state in which the administering device is supplied to a user. An actuation of the administering device is not possible in this state.

Figure 2:
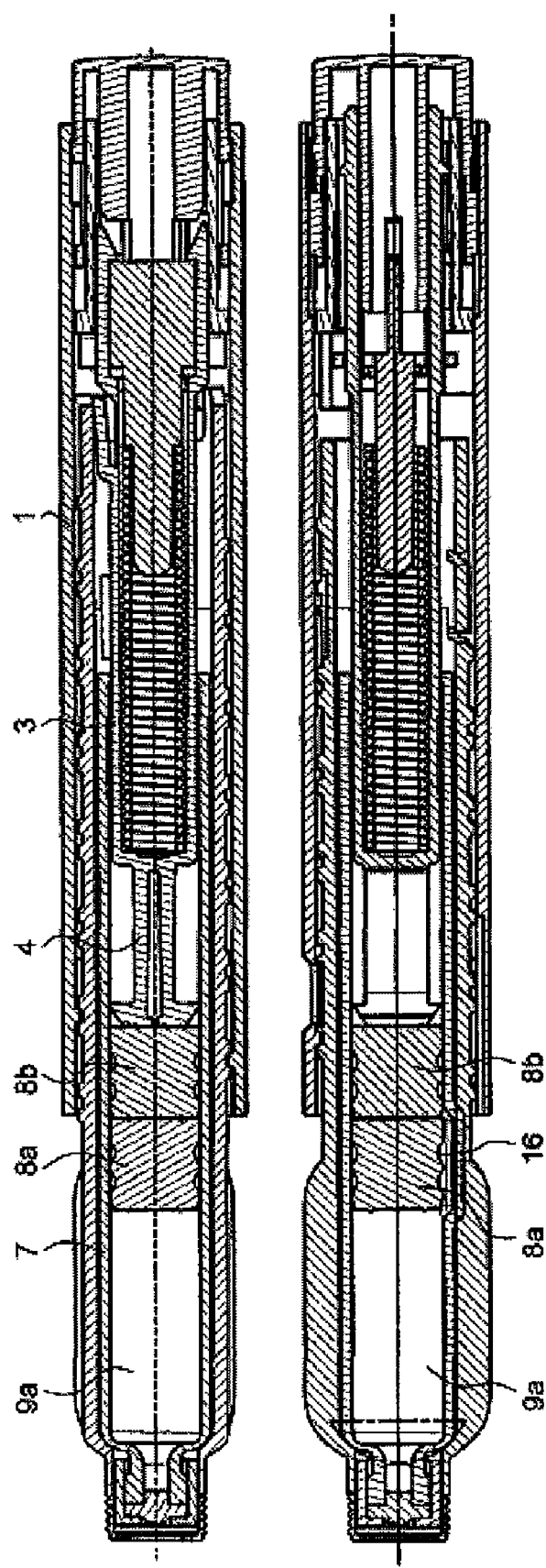
FIG. 2 shows the administering device in a state when mixing has taken place.

FIG. 2 shows the administering device in a state when mixing has taken place, in which state the active substance of the chamber 9a of the two-chamber carpule 7 has been mixed with the solvent of the chamber 9b. The completion of the mixing procedure can be indicated by a tactile, acoustic or visual signal. As is shown in FIG. 2, mixing was achieved by moving the stoppers 8a and 8b inside the carpule 7 until the stopper 8a comes to lie on a bypass 16 through which the solvent can flow into the chamber 9a and the stopper 8b comes to lie on the stopper 8a. For advancing the stoppers, the carpule holder 2 is screwed into the housing 1 such that the drive member, which in this state is at rest relative to the housing, moves the stoppers 8a and 8b relative to the carpule 7. To screw the carpule holder in, an inner thread is provided on the inside of the housing and an outer thread is provided on the outside of the carpule holder.

As can be seen in FIG. 2, the holding arms 4 have slipped from the proximal edge of the carpule 7 and have been moved radially inwardly in the direction of the longitudinal axis of the drive member. For this purpose, the ends of the holding arms 4 have oblique surfaces along which the holding arms 4 are deflected inwardly as soon as the proximal edge of the carpule 7 is pressed with sufficient force against the oblique surfaces, as is the case when the carpule holder 2 is screwed into the housing 1. The holding arms 4 move in toward each other and form a ram for the stopper 8b of the carpule 7. By the holding arms 4 abutting against the stopper 8b, the carpule 7 is further held in its defined position in the carpule holder 2, while the stoppers 8a and 8b are moved inside the carpule 7. Independently of this, the holding arms 4 form a press fit with the inside wall of the carpule 7, as they have radially outward pretensioning since having being bent radially inwardly. This press fit serves to hold the carpule in a defined or set position in the carpule holder.

After the mixing has taken place in the two-chamber carpule, it may be necessary for the chamber 9a, with the dissolved active substance, to have air removed from it before the active substance can be injected. For this purpose, an injection needle unit is mounted on the distal end of the carpule holder 2, such that a needle pierces the membrane of the carpule 7 and thus creates a fluid connection to the chamber 9a. Screwing in the carpule holder 2 slightly further leads to a further advance movement of the stoppers 8a and 8b, such that air located in the chamber 9a can escape. The advance movement is normally carried out until a small amount of the active substance 9a emerges from the needle of the injection needle unit. The completion of the air removal procedure, which also may be thought of and/or referred to as priming or a priming procedure, can be indicated by a tactile, acoustic or visual signal.

Figure 3:
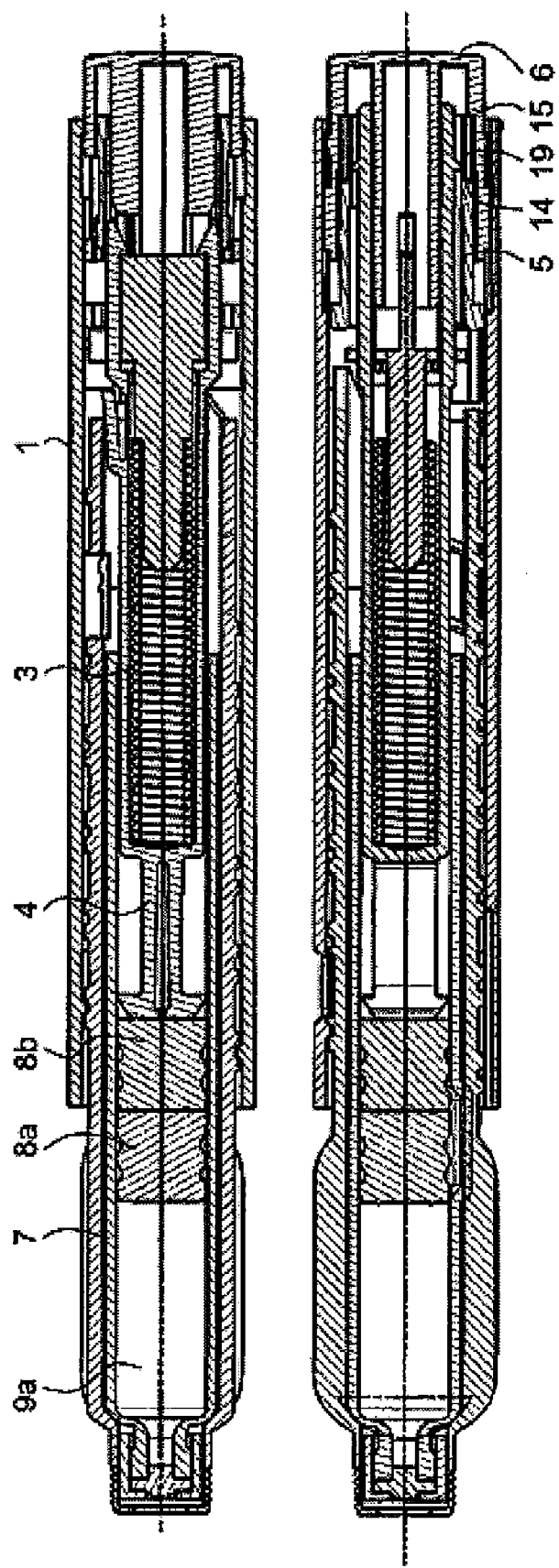
FIG. 3 shows the administering device in a state when air has been removed.

The state with the air removed in shown in FIG. 3. The injection needle unit is not shown. In the last screwing-in movement of the carpule holder 2 into the housing 1, in which air can also be removed from the carpule, the blocking ring 5 is moved from the blocking position to the release position. As is shown in FIGS. 6a-6d, the carpule holder for this purpose has an abutment 17, and the blocking ring has a counter-abutment 18. The abutment 17 of the carpule holder 2 is designed such that it abuts in the circumferential direction against the counter-abutment 18 of the blocking ring 5 during the rotation movement of the carpule holder. Upon further rotation of the carpule holder 2, the carpule holder carries the blocking ring 5 along with it, such that the blocking ring 5 is rotated relative to the housing 1 and to the trigger button 6. By this rotation movement, the blocking ring is moved from the blocking position to the release position. As is shown in FIG. 3, during the rotation the blocking abutment 14 of the blocking ring 5 is rotated away from the counter-abutment 15 of the trigger button 6 until the counter-abutment 15 lies opposite a groove or channel 19 of the blocking ring, inside which groove or channel 19 the counter-abutment 15 of the trigger button 6 can be moved in the longitudinal direction.

During the rotation of the blocking ring 5 by the carpule holder 2, the inner surfaces of the blocking ring 5, which prevent the snap-action arms 12 from disengaging from their snap-in position, are also rotated away from this position. In the release position of the blocking ring 5, the snap-action arms 12 lie opposite recesses in the sleeve face of the blocking ring 5. The blocking ring 5 is therefore also located in a release position with respect to the snap-action arms 12.

Figure 4:
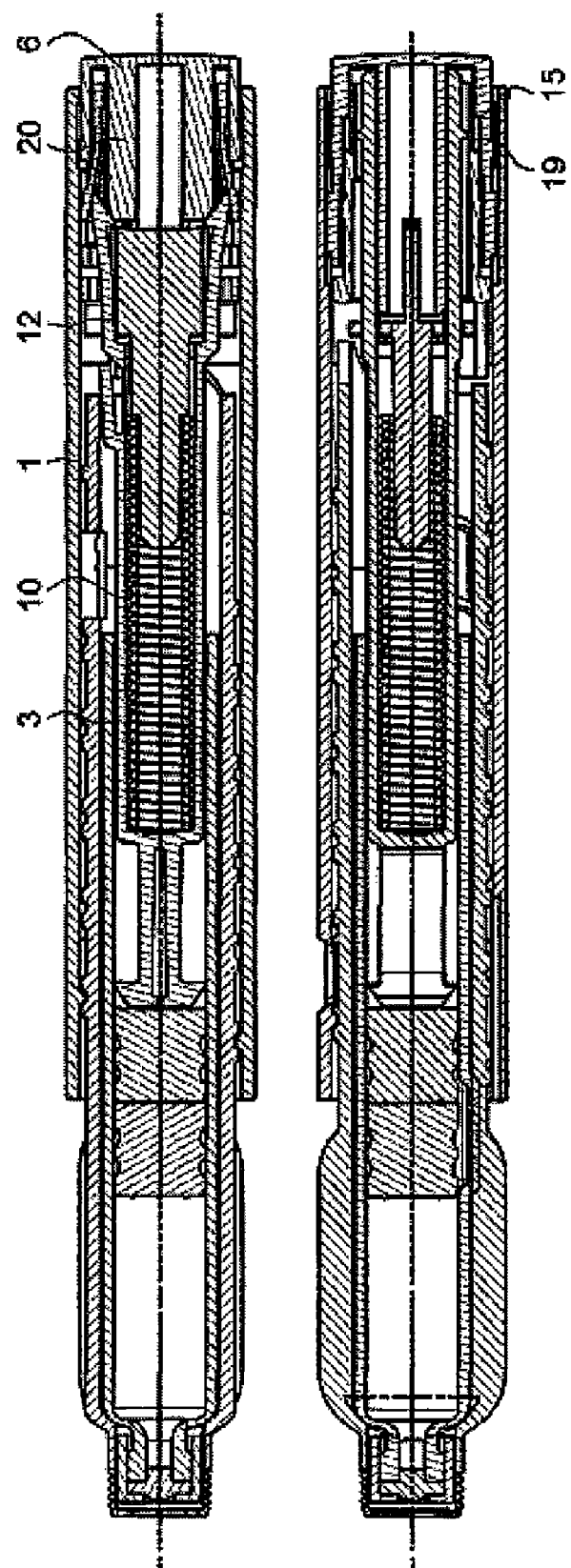
FIG. 4 shows the administering device in a triggered state.

FIG. 4 shows the administering device in a triggered state in which the trigger button 6 has been pressed into the housing 1 generally along the longitudinal axis of the housing 1. The counter-abutments 15 of the trigger button 6 have been moved inside the channels 19 of the blocking ring 5. The trigger button 6 has inwardly extending webs 20 which, when the trigger button is in the triggered or pushed-in state, bear against oblique surfaces on the proximal end of the snap-action arms 12 and spread the arms 12 radially outwardly as the trigger button 6 moves forward, such that the ends of the snap-action arms come to lie inside the recesses in the blocking ring 5. The securing of the drive member 3 on the housing element 11 is canceled by the spreading-open of the snap-action arms 12. In the triggered state, the spring force of the drive spring 10 begins to act and presses against the drive member 3.

Figure 5:
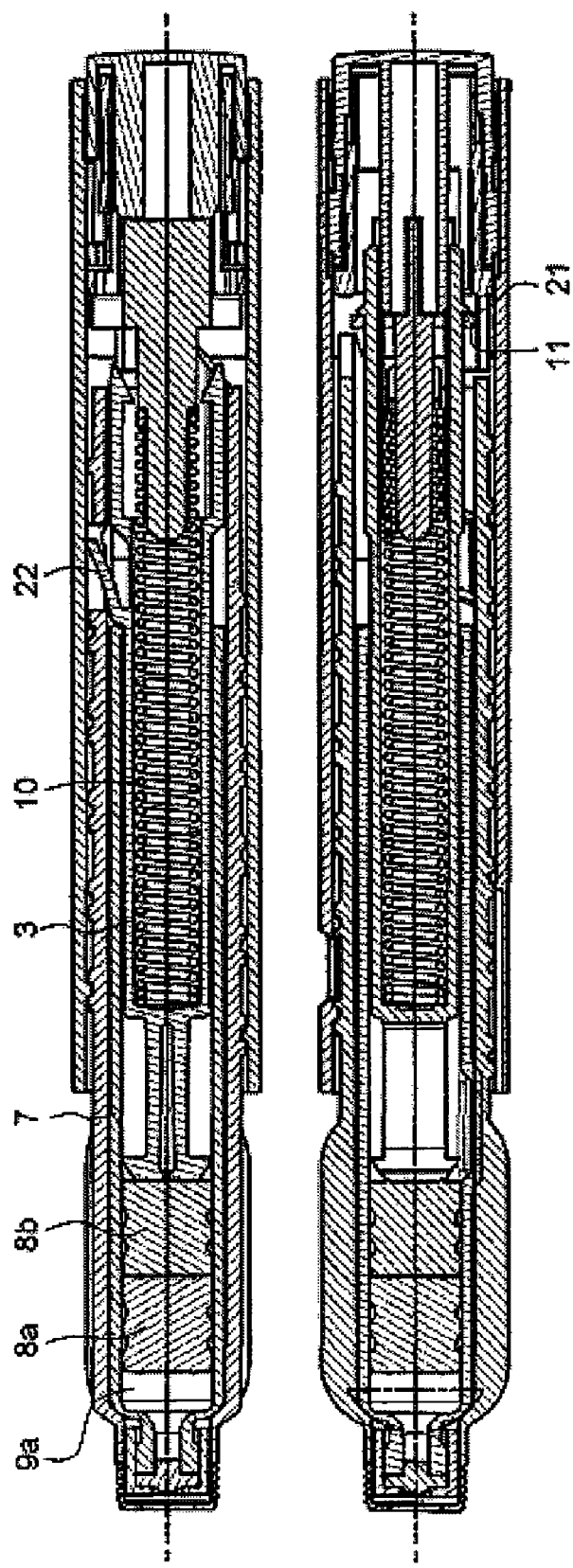
FIG. 5 shows the administering device in a state after a product has been discharged.
Figure 6A:
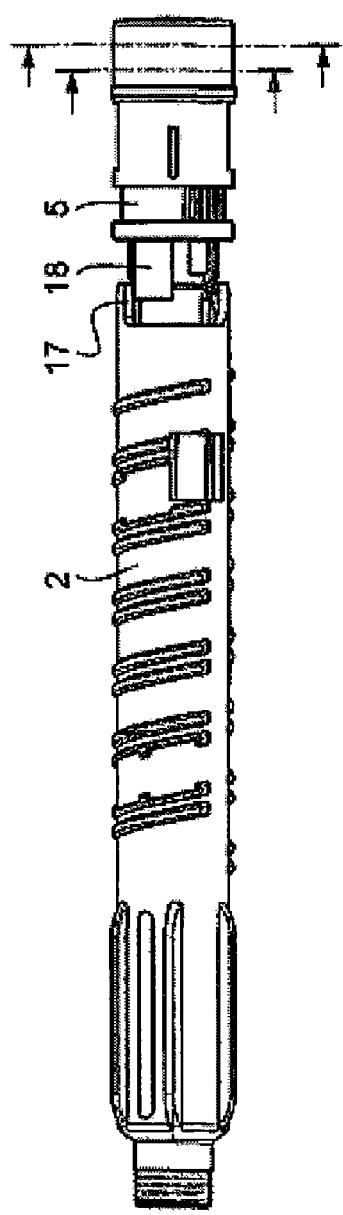
FIG. 6a is an inside view of the administering device in a blocking position.
Figure 6B:
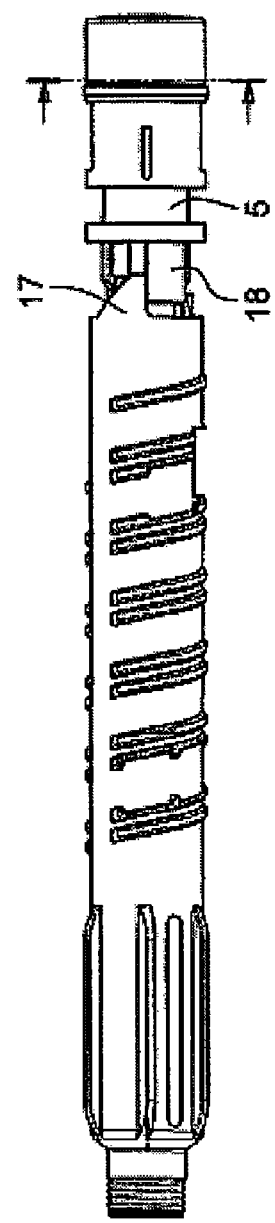
FIG. 6b is an inside view of the administering device in a release position.

As is shown in FIG. 5, the drive member 3 is moved forward relative to the carpule 7 by the force of the spring 10 and drives the stoppers 8a and 8b inside the carpule 7, such that the active substance is discharged from the chamber 9a. The drive spring 10 pushes the drive member 3 forward into the carpule until a projection 21, provided on the drive member 3, abuts against an edge of the housing element 11. As soon as the projection 21 abuts against the housing element 11, the discharging of the active substance is ended.

In the illustrative embodiment shown, a flexible arm 22, provided on the drive member 3, protrudes into and/or lodges in a recess in the carpule holder, when the discharging has ended, and serves to block or prevent a movement of the drive member 3 in the proximal direction. Moreover, when it catches in the recess of the carpule holder, the arm 22 produces an acoustic noise, which indicates that the discharging has been completed.

FIGS. 7a and 7b show another embodiment of an administering device with a blocking mechanism according to the present invention. In this variant, the blocking mechanism is arranged on the actuation element, which is in the form of the trigger button. As is shown in FIG. 7a, a locking arm 23 protrudes or extends from the trigger button 6 in the longitudinal direction of the administering device. The locking arm 23 and the trigger button 6 are one piece or integrally connected. A blocking abutment 24, which abuts in the longitudinal direction against a longitudinal abutment of the housing element 11, is provided on the locking arm 23. Because of the contact of the blocking abutment 24 with the longitudinal abutment 25, the trigger button 6 cannot be pressed in the longitudinal direction into the housing 1.

In FIG. 7b, the carpule holder 2 has already been screwed into the housing 1. The carpule holder 2 is screwed into the housing until an abutment 17' of the carpule holder abuts in the circumferential direction against a counter-abutment 18' of the locking arm 23 of the trigger button 6. Upon further rotation of the carpule holder 2, the locking arm 23 is deflected in the circumferential direction relative to its rest position, since the abutment 17' acts against the counter-abutment 18'. The blocking abutment of the trigger button 6 is in this way deflected from its blocking position relative to the longitudinal abutment 25 of the housing element 11 and comes to lie opposite a recess in the housing element 11. The blocking mechanism for blocking the trigger button 6 is now located in a release position in which the trigger button 6 can be pressed into the housing 1 along the longitudinal axis. The blocking abutment 24 is guided through the recess in the housing element 11.

In this embodiment, the carpule holder 2 has a catch mechanism with which it locks relative to the housing as soon as the blocking mechanism is in a release position, such that a reverse rotation of the carpule holder and consequently a renewed blocking of the trigger button are prevented.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An apparatus for administering a substance, comprising a housing, an administering mechanism accommodated in the housing, an actuation element for actuating the administering mechanism, a receptacle for holding the substance, wherein the receptacle is rotatable relative to the housing and receives a two-chamber carpule, each chamber containing a constituent of the substance, the constituents being able to be mixed by rotation of the receptacle, and a lock for releasably locking the actuation element, wherein the lock can be unlocked by rotating the receptacle.

2. The apparatus for administering a substance according to claim 1, wherein the receptacle comprises an abutment and the lock comprises a counter-abutment, the abutment and counter-abutment interacting to move the lock from locked to unlocked.

3. A device for administering a fluid product, comprising:
a housing for receiving an administering mechanism,
an actuation element for actuating the administering mechanism,
a receptacle for receiving the fluid product, wherein the receptacle is rotatable releative to the housing and receives a two-chamber carpule, each chamber containing a constituent of the fluid product, the constituents being able to be mixed by rotation of the receptacle, and
a blocking mechanism for blocking the actuation element, wherein
the blocking mechanism is movable from a blocking position to a release position by rotation of the receptacle.

4. The device for administering a fluid product as claimed in claim 3, wherein the receptacle has an abutment and the blocking mechanism has a counter-abutment, which interact to move the blocking mechanism from the blocking position to the release position.

5. The device for administering a fluid product as claimed in claim 3, wherein, in the release position of the blocking mechanism, the actuation element is movable relative to the housing along a longitudinal axis of the housing.

6. The device for administering a fluid product as claimed in claim 3, wherein the blocking mechanism is on the actuation element.

7. The device for administering a fluid product as claimed in claim 6, wherein the blocking mechanism comprises a flexible arm which can deflect relative to the actuation element in the circumferential direction of the longitudinal axis.

8. The device for administering a fluid product as claimed in claim 3, wherein the blocking mechanism is rotatable relative to the actuation element.

9. The device for administering a fluid product as claimed in claim 8, wherein the blocking mechanism has a blocking abutment which, in the blocking position, abuts against a longitudinal abutment on one of the actuation element, the housing, or a structure fixed to the housing.

10. The device for administering a fluid product as claimed in claim 9, wherein the blocking mechanism comprises a locking means for, in the blocking position, locking a drive member against forward movement.

11. The device for administering a fluid product as claimed in claim 3, wherein the release position of the blocking mechanism corresponds to a position of the two-chamber carpule after mixing has taken place.

12. A device for administering a fluid product, comprising:
a housing for receiving an administering mechanism;
an actuation element for actuating the administering mechanism;
a receptacle for receiving the fluid product;
a blocking mechanism for blocking the actuation element, wherein the receptacle is rotatable relative to the housing and the blocking mechanism is movable from a blocking position to a release position by rotation of the receptacle; and a catch mechanism which locks the receptacle relative to the housing in the release position of the blocking mechanism.

13. The device for administering a fluid product as claimed in claim 12, wherein the receptacle receives a two-chamber carpule, each chamber containing a constituent of the fluid product, the constituents being able to be mixed by rotation of the receptacle.

* * * * *